(12) United States Patent
Bonnick et al.

(10) Patent No.: US 10,241,035 B2
(45) Date of Patent: Mar. 26, 2019

(54) SPECTROPHOTOMETRIC SENSORS AND METHODS OF USING SAME

(71) Applicant: Evoqua Water Technologies Limited, Sevenoaks (GB)

(72) Inventors: David Macdonald Bonnick, Heathfield (GB); Michael Brooks, The Elms Lodge (GB)

(73) Assignee: Evoqua Water Technologies LLC, Pittsburgh, PA (US)

( * ) Notice: Subject to any disclaimer, the term of this patent is extended or adjusted under 35 U.S.C. 154(b) by 313 days.

(21) Appl. No.: 15/101,483

(22) PCT Filed: Dec. 9, 2014

(86) PCT No.: PCT/EP2014/077037
§ 371 (c)(1),
(2) Date: Jun. 3, 2016

(87) PCT Pub. No.: WO2015/086592
PCT Pub. Date: Jun. 18, 2015

(65) Prior Publication Data
US 2016/0313239 A1 Oct. 27, 2016

(30) Foreign Application Priority Data

Dec. 12, 2013 (GB) .................... 1322026.4

(51) Int. Cl.
| | |
|---|---|
| *G01N 21/33* | (2006.01) |
| *C02F 1/467* | (2006.01) |
| *C02F 1/00* | (2006.01) |
| *C02F 1/50* | (2006.01) |

(52) U.S. Cl.
CPC ............ *G01N 21/33* (2013.01); *C02F 1/008* (2013.01); *C02F 1/4674* (2013.01); *C02F 1/50* (2013.01); *C02F 2201/4612* (2013.01); *C02F 2209/29* (2013.01); *C02F 2303/04* (2013.01); *G01N 2201/062* (2013.01); *G01N 2201/08* (2013.01)

(58) Field of Classification Search
None
See application file for complete search history.

(56) References Cited

U.S. PATENT DOCUMENTS

| | | | | |
|---|---|---|---|---|
| 4,500,404 A | * | 2/1985 | Tucker .................. | C02F 1/4674 204/263 |
| 6,051,437 A | * | 4/2000 | Luo ........................ | B82Y 15/00 422/82.05 |
| 6,093,292 A | * | 7/2000 | Akiyama .............. | C02F 1/4618 204/263 |
| 9,015,003 B2 | * | 4/2015 | Wolfe .................... | G01N 33/18 702/182 |
| 2003/0098419 A1 | | 5/2003 | Ji et al. | |
| 2007/0138401 A1 | | 6/2007 | Tokhtuev et al. | |

(Continued)

FOREIGN PATENT DOCUMENTS

| | | |
|---|---|---|
| EP | 0885986 A2 | 12/1998 |
| GB | 2312892 A | 11/1997 |

*Primary Examiner* — Chester T Barry

(57) ABSTRACT

Spectrophotometric sensors for measuring the concentration of various solutions are disclosed. Methods for controlling the introduction of disinfectants using such sensors for water treatment are also disclosed. Hypochlorite strength is monitored in at least some embodiments.

16 Claims, 13 Drawing Sheets

(56) References Cited

U.S. PATENT DOCUMENTS

| | | | |
|---|---|---|---|
| 2008/0130003 A1* | 6/2008 | Kuroda | G01N 21/554 356/445 |
| 2009/0219513 A1* | 9/2009 | Shakespeare | G01J 3/10 356/51 |
| 2013/0286397 A1* | 10/2013 | Witinski | G01J 3/42 356/409 |
| 2015/0077756 A1* | 3/2015 | Campbell | G01N 33/1826 356/450 |
| 2016/0136320 A1* | 5/2016 | Tucker | A61L 12/122 424/10.32 |

* cited by examiner

SPECTROPHOTOMETRIC SENSORS AND METHODS OF USING SAME

CROSS-REFERENCE TO RELATED APPLICATION

This application claims priority to U.K. Patent Application Serial No. 1322026.4, filed on Dec. 12, 2013 and titled "HYPOCHLORITE STRENGTH MONITOR," the entire disclosure of which is hereby incorporated herein by reference in its entirety for all purposes.

FIELD OF THE DISCLOSURE

Aspects relate generally to water treatment and, more particularly, to devices, systems and methods for measuring and controlling the introduction of disinfectants.

BACKGROUND

It is beneficial to monitor the strength of hypochlorite solutions used for disinfection purposes. Commercial hypochlorite degrades over time as a function of temperature and in the presence of certain impurities. It is also commonly diluted prior to dosing and it is beneficial to know the strength of the diluted solution. On-site electrolytic generated hypochlorite may also vary in strength and it is useful to know the concentration for the purposes of process optimization.

Many compounds absorb ultraviolet (UV) or visible (Vis.) light. The diagram 500 of FIG. 5 shows a beam of monochromatic radiation 510 of radiant power $P_0$, directed at a sample solution 520. Absorption takes place and the beam of radiation leaving the sample 530 has a reduced radiant power P.

Transmittance may be calculated according to the following equations:

Transmittance, $T=P/P_0$; and

% Transmittance, $\%T=100\,T$.

Absorbance may be calculated according to the following equations:

Absorbance, $A=\log 10\, P_0/P$;

$A=\log 10\, 1/T$;

$A=\log 10\, 100/\%\,T$; and $A=2-\log 10\%\, T$.

The relationship between absorbance and transmittance is illustrated in FIG. 6. If all the light passes through a solution without any absorption, then absorbance is zero, and percent transmittance is 100%. If all the light is absorbed, then percent transmittance is zero, and absorption is infinite.

SUMMARY

In accordance with one or more aspects, a spectrophotometric hypochlorite sensor may comprise a first source of monochromatic radiation configured to produce an emitted light, a sample chamber configured and positioned to receive the emitted light and contain a sample comprising hypochlorite through which the emitted light passes to produce a partially absorbed light, a detector configured and positioned to receive the partially absorbed light and generate an input signal in response to receiving the partially absorbed light, and a processor configured to receive the input signal from the detector, correlate the input signal to a hypochlorite concentration of the sample, and generate an output signal indicative of the hypochlorite concentration of the sample.

In accordance with one or more aspects, a water treatment system may include a source of disinfectant comprising hypochlorite, a source of water to be treated, the spectrophotometric hypochlorite sensor described above and configured to detect a hypochlorite concentration of the disinfectant, wherein the sample chamber is positioned downstream of the source of disinfectant and configured to receive a portion of the disinfectant as the sample, and a valve positioned between the source of disinfectant and the source of water to be treated, the valve responsive to the output signal and configured to regulate introduction of the disinfectant to the waste influent to produce treated water.

In accordance with one or more aspects, a hypochlorite strength monitoring system may comprise an onsite hypochlorite generator comprising an electrolytic cell, and the spectrophotometric hypochlorite sensor described above and constructed and arranged to measure a hypochlorite concentration of a product stream at an outlet of the onsite hypochlorite generator.

In accordance with one or more aspects, a method for regulating disinfection of water to be treated may comprise emitting an electromagnetic beam having a first radiant power through a sample of disinfectant to produce a partially absorbed electromagnetic beam, measuring a second radiant power of the partially absorbed electromagnetic beam, calculating a concentration of the disinfectant based, at least in part, on the first radiant power and the second radiant power, and adjusting a valve configured to regulate introduction of the disinfectant to the water to be treated based, at least in part, on the calculated disinfectant concentration.

In accordance with one or more aspects, a method for treating water may comprise fluidly connecting a source of a disinfectant comprising up to about 15% by weight hypochlorite to the water, and regulating disinfection of the water according to the method described above.

In accordance with one or more aspects, a method of facilitating water treatment may comprise providing the spectrophotometric hypochlorite sensor described above at a water treatment site comprising a source of hypochlorite in fluid communication with water to be treated.

Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. Where technical features in the figures, detailed description or any claim are followed by references signs, the reference signs have been included for the sole purpose of increasing the intelligibility of the figures and description. In the figures, each identical or nearly identical component that is illustrated in various figures is represented by a like numeral. For purposes of clarity, not every component may be labeled in every figure. In the figures:

DETAILED DESCRIPTION

In accordance with one or more embodiments, spectrophotometric devices, methods, and systems may use non-peak UV/Vis absorbance to determine disinfectant concentration, for example, hypochlorite concentration, in aqueous solutions. This enables the use of a light source from a low cost UV apparatus, such as a stable Light Emitting Diodes (LED), and permits the measurement of high concentrations, for example from 0.1% to 15% wt/wt, which would otherwise completely absorb the transmitted radiation at absorbance peak wavelengths.

According to one or more embodiments, an inline hypochlorite sensor is provided for continuous measurement of hypochlorite strength based on spectrophotometry. The sensor comprises a source of monochromatic radiation, also referred to as an emitter. An LED may emit the radiation or light. Alternatively, the emitter may be a laser or other suitable source. The light may be emitted at a non-peak absorbance wavelength of the disinfectant being measured. One skilled in the art would understand the peak absorbance wavelength for hypochlorite to be specifically about 290 nm, or more generally a range from 280 nm to 300 nm. A non-peak wavelength would therefore be understood to be a wavelength outside of the range of 280 nm to 300 nm. For example, according to one or more embodiments, a monochromatic beam may have a wavelength in the range of about 350 nm to about 410 nm. According to one or more specific embodiments, the wavelength may be in the range of about 380 nm to about 395 nm. Use of a wavelength where the absorption by hypochlorite is relatively lower allows for measurements to be taken both accurately and cost-efficiently over a large range of concentrations. An obtained correlation of 0.9878 between the known and measured hypochlorite concentrations, as described in Example One, below, demonstrates the novel discovery that the Beer-Lambert law can be applied at non-peak wavelengths.

This disclosure is not limited to the measurement of hypochlorite in solution. Other chemicals could be monitored including various chlorine species, for example, chlorine dioxide. An appropriate wavelength would be determined based on the compound of interest.

Figure 1:
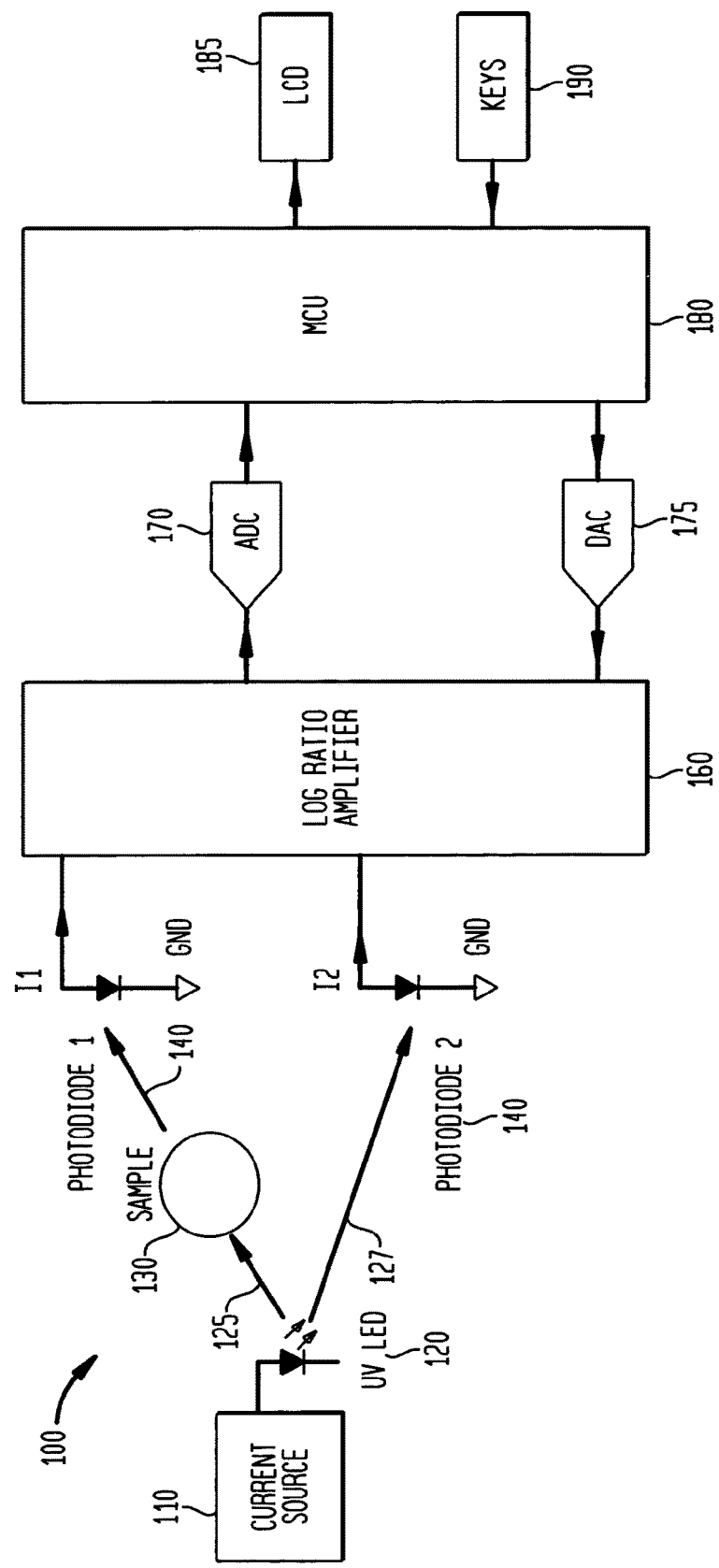
FIG. 1 presents a schematic of a spectrophotometric sensor in accordance with one or more embodiments.

According to one or more embodiments, an apparatus is provided comprising a UV LED of an appropriately specified wavelength, a measuring cell, and two photodiode detectors that are capable of converting light into a voltage or current, as shown in FIG. 1.

In the sensor 100 shown in FIG. 1, a ratio measurement may be taken to compensate for changes in emitter 120 output power. This arrangement includes two light paths 125 and 127, and two detectors 140. A log ratio amplifier 160 may be used to give a linear output from the two detector 140 signals.

A current source 110 delivers power to an ultraviolet or visible LED 120. The light is split and travels down paths 125 and 127. The first path 125 is directed through a sample 130 where some of the light is absorbed and measured by the photodiode 140. The signal voltage from the photodiode may then be sent to an amplifier 160 and from there to an analog to digital convertor 170. The converted signal is then sent to processor 180 where either the voltage or a calculated concentration value can be displayed on an output display 185. User input may be delivered through keyboard 190. Signals from the processor 180 to other components of the sensor may be delivered after digital to analog conversion 175.

Figure 2:
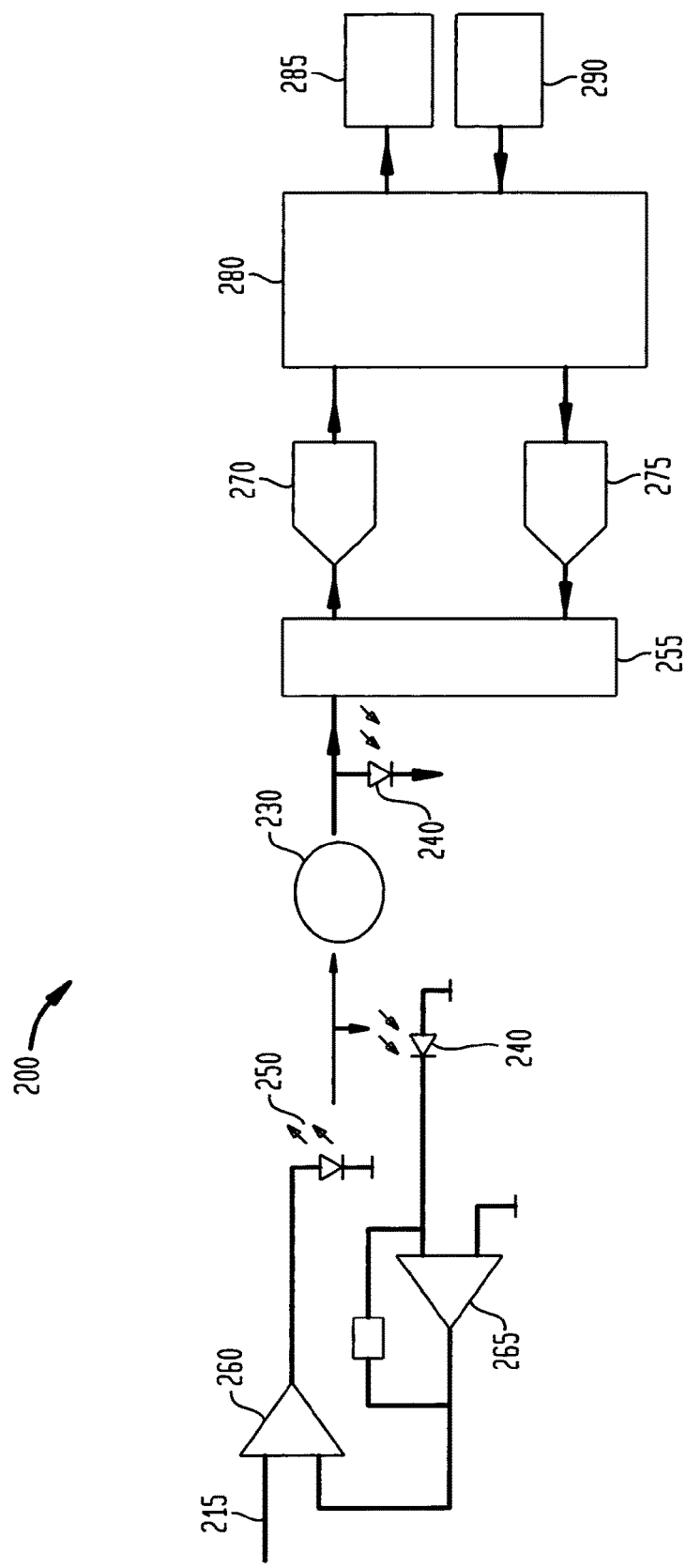
FIG. 2 presents a schematic of a spectrophotometric sensor in accordance with one or more embodiments.
Figure 4:
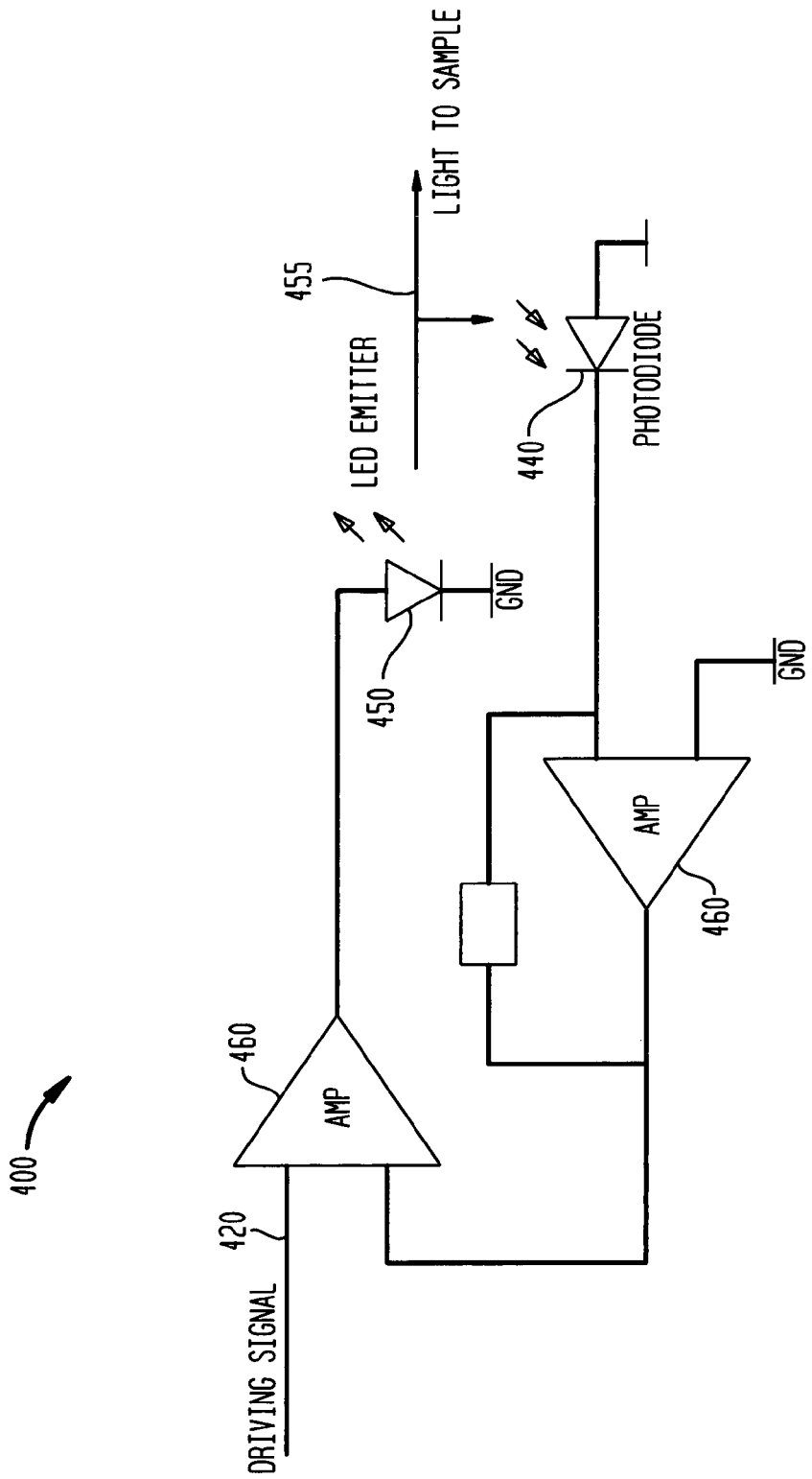
FIG. 4 presents a schematic of a spectrophotometric sensor detail in accordance with one or more embodiments.
Figure 5:
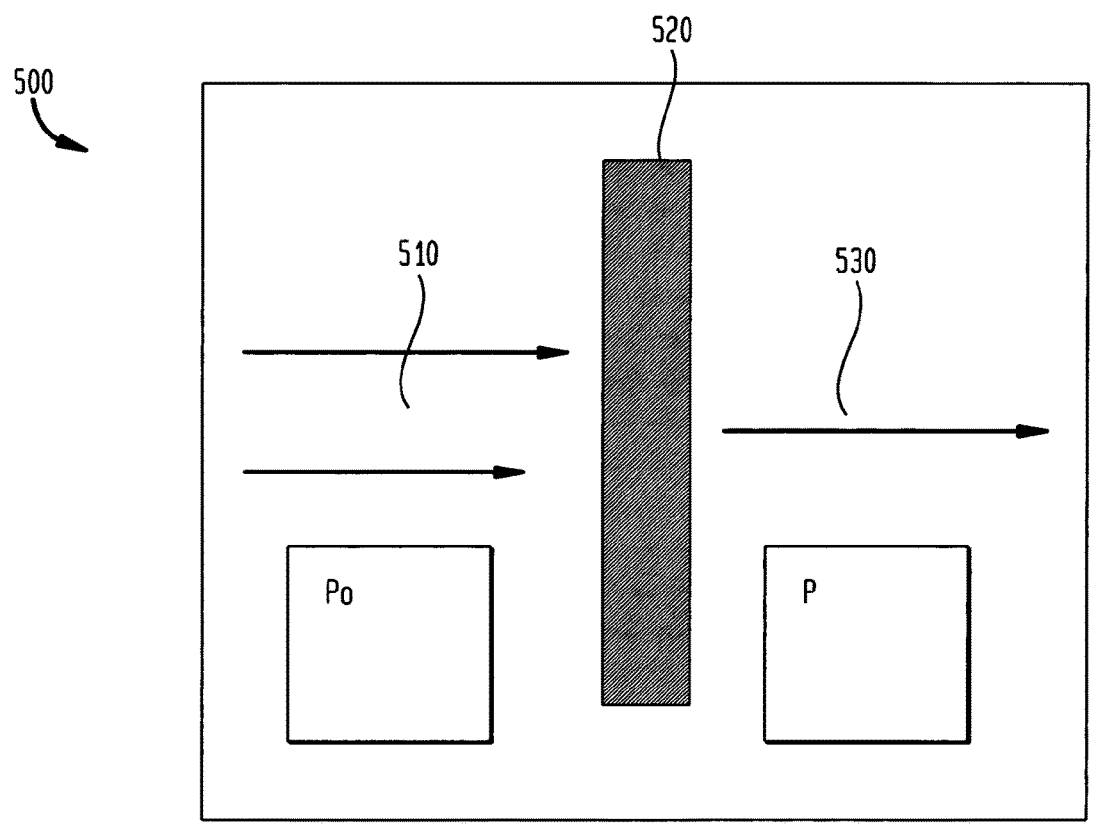
FIG. 5 presents a diagram illustrating the principles of absorbance and transmittance.
Figure 6:
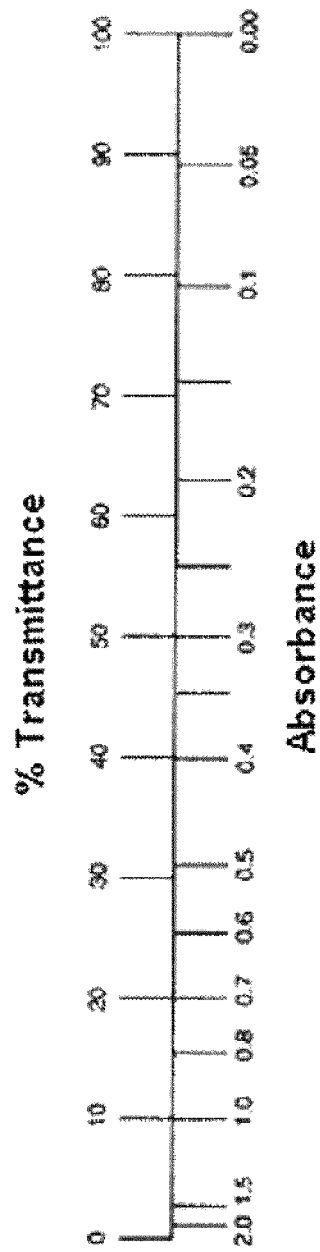
FIG. 6 presents a diagram illustrating the relationship between absorbance and transmittance values.

According to one or more embodiments, an alternative embodiment is provided which uses a single self-monitoring emitter 400, as shown in FIG. 4. A single self-monitoring emitter is incorporated into a sensor 200 as shown in FIG. 2. In the arrangement of FIG. 4, a small fraction of the output light 455 from LED emitter 450 is diverted to a detector diode 440, and a feedback amplifier 460, which receives a driving signal 420, is used to maintain a constant optical output. The mechanical arrangement is simplified as only a single input to a log amplifier is required to give an output linear with concentration, as shown in FIG. 2.

FIG. 2 depicts a sensor 200 incorporating the self-monitoring emitter. A reference voltage 215 amplified by an amplifier 260 delivers power to the LED 250 at a constant output. The light from emitter 250 is then split with a fraction of the light diverted to a photodiode 240, which then delivers a voltage signal to amplifier 265. The remaining light passes through the sample 230 and is measured by another photodiode 240. A voltage signal from the photodiode 240, representative of the absorbance of the sample 230, may be sent to a log ratio amplifier 255 and, from there, sent to an analog to digital convertor 270. The converted signal is then sent to processor 280 where either the voltage or a calculated concentration value may be displayed on an output display 285. User input may be delivered through keyboard 290. Signals from the processor 280 to other components of the sensor 200 may be delivered after digital to analog conversion 275.

Figure 3:
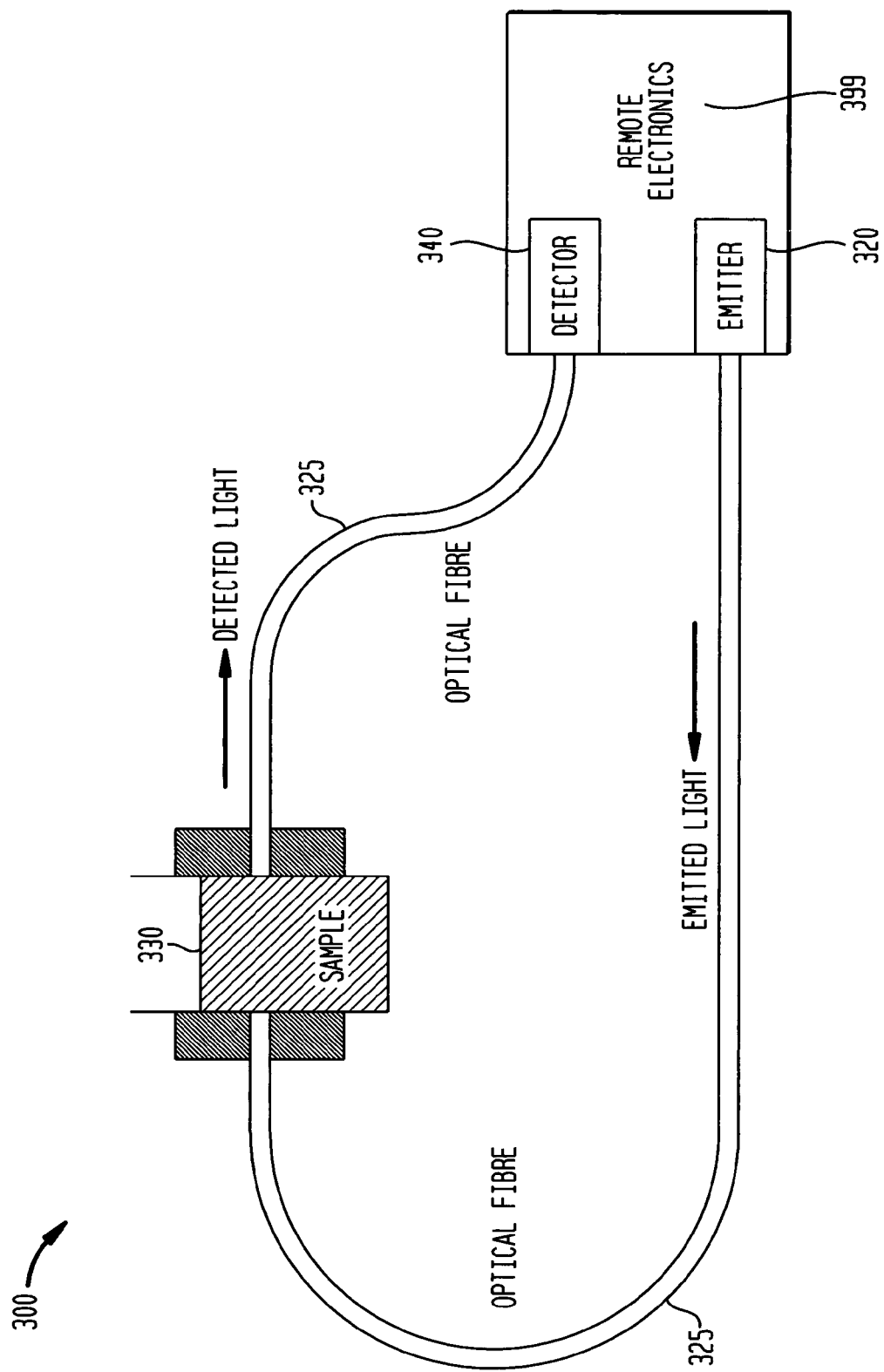
FIG. 3 presents a schematic of a spectrophotometric sensor detail in accordance with one or more embodiments.

According to one or more embodiments, a fiber optic cable 325 is employed in the sensor 300 to guide the light from the emitter 320 to the sample 330, and back to the detector 340. This arrangement is shown in FIG. 3. This allows the measurement electronics 399 to be located at a different location to the sample 330 being measured. This arrangement may be advantageous where an explosive atmosphere could be present in the sample area, as there are no electrical connections or ignition sources near the sample.

According to one or more embodiments, the sensor may be configured to be handheld. In this embodiment, a sample of disinfectant is collected and placed into a device where it is measured. Alternatively, the handheld sensor may be introduced to a sample of solution to be tested. This handheld system comprises generally the same components described in above embodiments, only configured and arranged to fit into a handheld device.

According to one or more embodiments, the apparatus could use multiple LEDs comprising different wavelengths or spectrums to determine mixtures of substances or to determine concentrations of substances in a matrix, for example residual chlorine in drinking water.

According to one or more embodiments, the spectrophotometric sensor discussed above may be incorporated into a water treatment system. A disinfectant source may comprise hypochlorite. The hypochlorite may be stored or generated on site. The disinfectant is used to treat a water stream. Knowledge of the hypochlorite concentration aids in properly dosing the water stream. To this end, the spectrophotometric sensor may be positioned to measure a sample of hypochlorite to determine its concentration prior to introducing the disinfectant to the treatment stream. Alternatively, the disclosed sensors may monitor the concentration of disinfectant in a dosed stream. One or more process flow rates may be adjusted in response to the detected concentration.

According to one or more embodiments, a valve or similar structure may be positioned between the source of disinfectant and the water to be treated. The valve may be used to regulate introduction of disinfectant to the water in response to the reading of the sensor. The sensor may, for example, produce an output signal indicative of the concentration to the valve. The valve may open or close a desired amount in response to the signal from the valve. The valve may be operated manually or automated. The concentration of disinfectant may be monitored prior to or subsequent to introduction to water to be treated.

Figure 12:
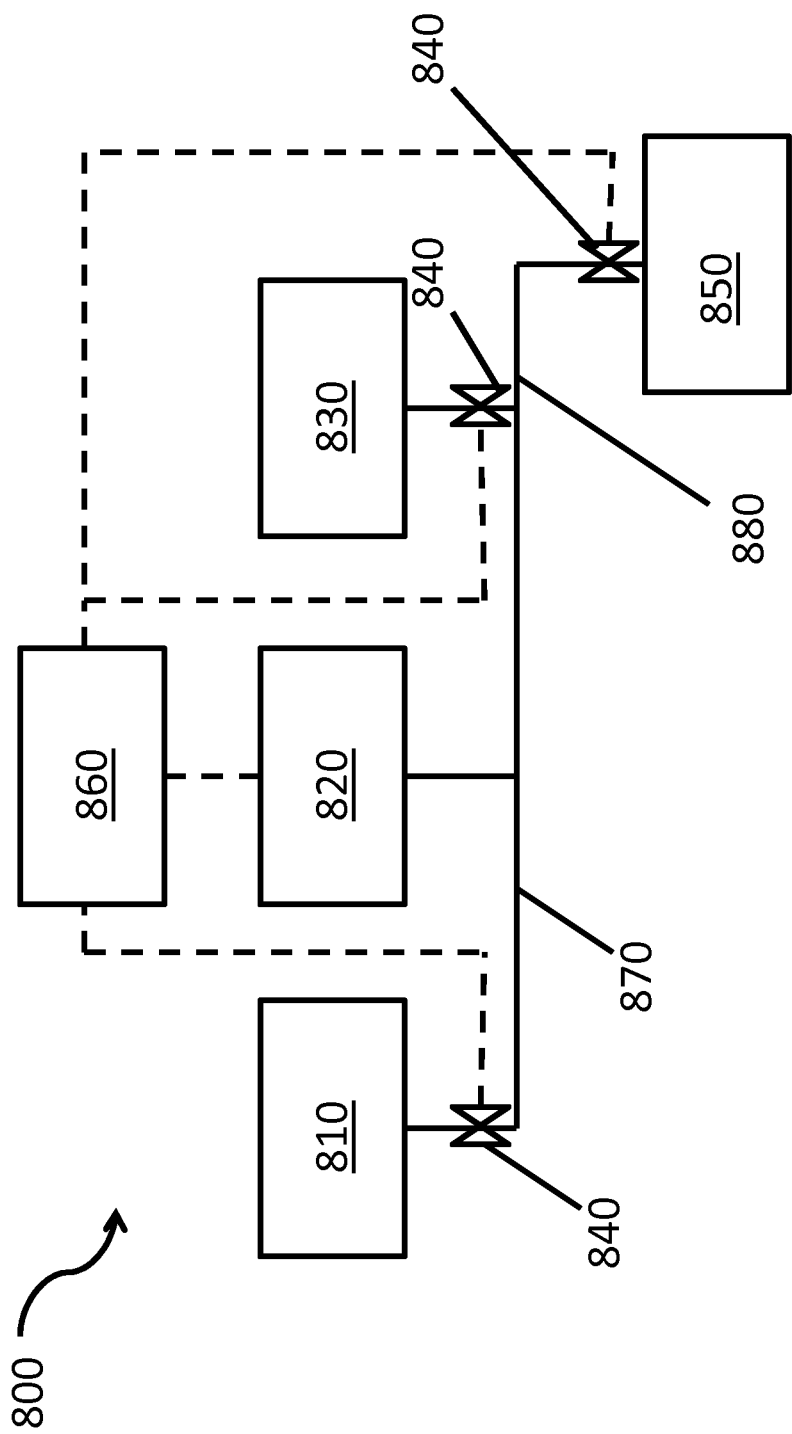
FIG. 12 presents a schematic of an embodiment of a system incorporating a spectrophotometric sensor.
Figure 13:
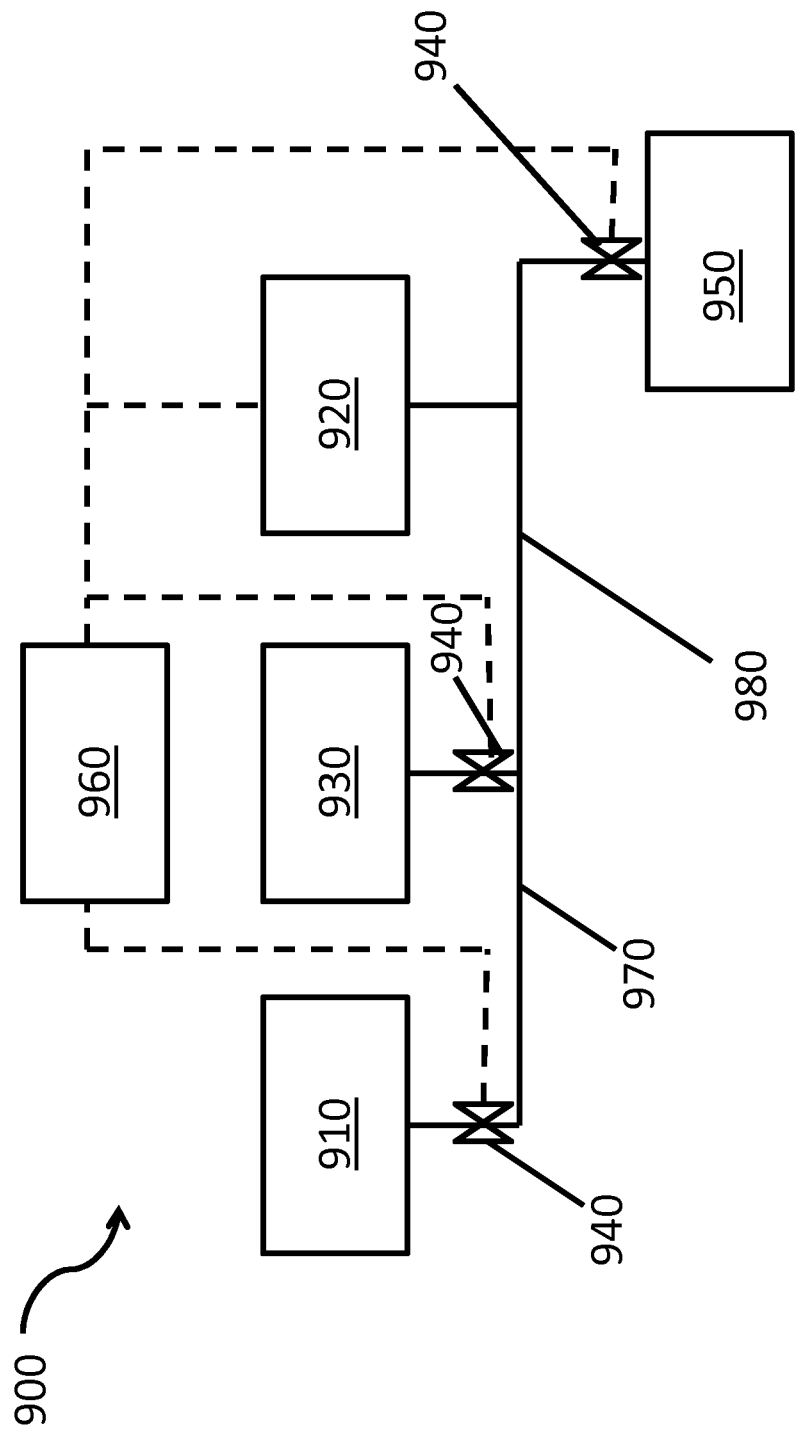
FIG. 13 presents a schematic of an embodiment of a system incorporating a spectrophotometric sensor.

According to one or more embodiments, the hypochlorite monitoring apparatus may be used in combination with an on-site electro-chlorination hypochlorite generating system to control and monitor the process as shown in FIGS. 12 and 13. In an on-site electro-chlorination hypochlorite generating apparatus, an aqueous sodium chloride solution is converted to sodium hypochlorite in an electrolytic cell. This is preferable to storing large containers of hypochlorite solution that can degrade over time. It is also safer than transporting and storing chlorine gas.

As shown in FIG. 12, the strength of the generated hypochlorite solution exiting from an outlet of the generator 810 may be monitored by the disclosed sensor 820. The system may further include a source of diluting water 830. The diluting water 830 may be mixed with the generated hypochlorite solution 870 to provide a diluted product stream 880. According to at least one embodiment, the sensor 820 may be positioned to measure an undiluted product stream prior to mixing with the diluting water. Alternatively, as shown in FIG. 13 the sensor 920 may be positioned to measure a diluted product stream 980 after the generated hypochlorite solution 970 is mixed with the diluting water 930. In either embodiment, the measured concentration from the sensor 820 or 920 may be used as feedback and in conjunction with, for example, a control system 860 or 960 and/or a valve 840 or 940, to regulate either the amount of diluting water introduced to form the diluted product stream, or the amount of diluted product stream introduced to a stream 850 or 950 to be treated.

According to one or more embodiments, a method to measure the concentration of hypochlorite is disclosed. This method comprises adding a solution of hypochlorite to a measuring cell, directing a beam of monochromatic radiation through the measuring cell containing the hypochlorite solution to a photo-diode detector, measuring the voltage from the photodiode detector and correlating the voltage from the photo-diode detector to the hypochlorite concentration of the hypochlorite solution in the measuring cell. The beam may be emitted from a light emitting diode. The light may be emitted at a wavelength of about 350 nm to 410 nm. The light may be emitted at a wavelength of about 380 nm to 395 nm. The disinfectant concentration may be a hypochlorite concentration in the range of about 0.1% to about 15% by weight.

According to one or more embodiments, water may be treated by connecting a source of disinfectant, such as hypochlorite, having a concentration of up to 15% by weight hypochlorite to the water to be treated, and regulating disinfection of the water.

According to one or more embodiments, a method of facilitating water treatment may comprise providing the disclosed hypochlorite sensor at a water treatment site comprising a source of hypochlorite in fluid communication with water to be treated. The method may further comprise providing an onsite hypochlorite generator upstream of the sensor as the source of hypochlorite.

In some embodiments, the hypochlorite may be used as a reactant, such as for the production of chlorine dioxide. The disclosed sensors may be used to monitor the reactant concentration fed to a reaction chamber for improved process control and efficiency.

The function and advantages of these and other embodiments will be more fully understood from the following non-limiting examples. The examples are intended to be illustrative in nature and are not to be considered as limiting the scope of the embodiments discussed herein.

EXAMPLE 1

An experiment was performed to confirm that hypochlorite behaves according to the Beer-Lambert Law even at non-peak wavelengths. The scientific basis behind this disclosure is the Beer-Lambert Law which proposes that the absorbance of an active substance solution is linear to the concentration of the substance. More precisely:

$$A = \varepsilon \times b \times c$$

Where, A is absorbance (no units, since $A = \log 10\ (I_o/I)$), $\varepsilon$ is the molar absorptivity with units of L mol$^{-1}$cm$^{-1}$, b is the path length of the sample, c is the concentration of the compound in solution, expressed in mol L$^{-1}$.

This investigation focuses on wavelengths away from the absorbance peak, where the absorbance is significantly lower and, therefore, high concentrations can be measured more accurately.

Samples having a known hypochlorite concentration were prepared using an iodometric titration method. 50 ml distilled water followed by 5 g of acetic acid and a tablet of potassium iodide (1 g) were placed in a flask. The chosen sample volume was 5 ml (V) and was poured in the mix and stirred to provide a unified solution. Standard sodium thiosulphate was added from a burette, until the brown color from the liberated iodine was discharged and the solution was crystal clear. The volume of thiosulphate used for the discharge was recorded (T). The following general equation was used to calculate the hypochlorite strength [5]:

$$\text{mg/l as } Cl_2/L = (T \times 3.545 \times 1000)/V$$

Figure 7:
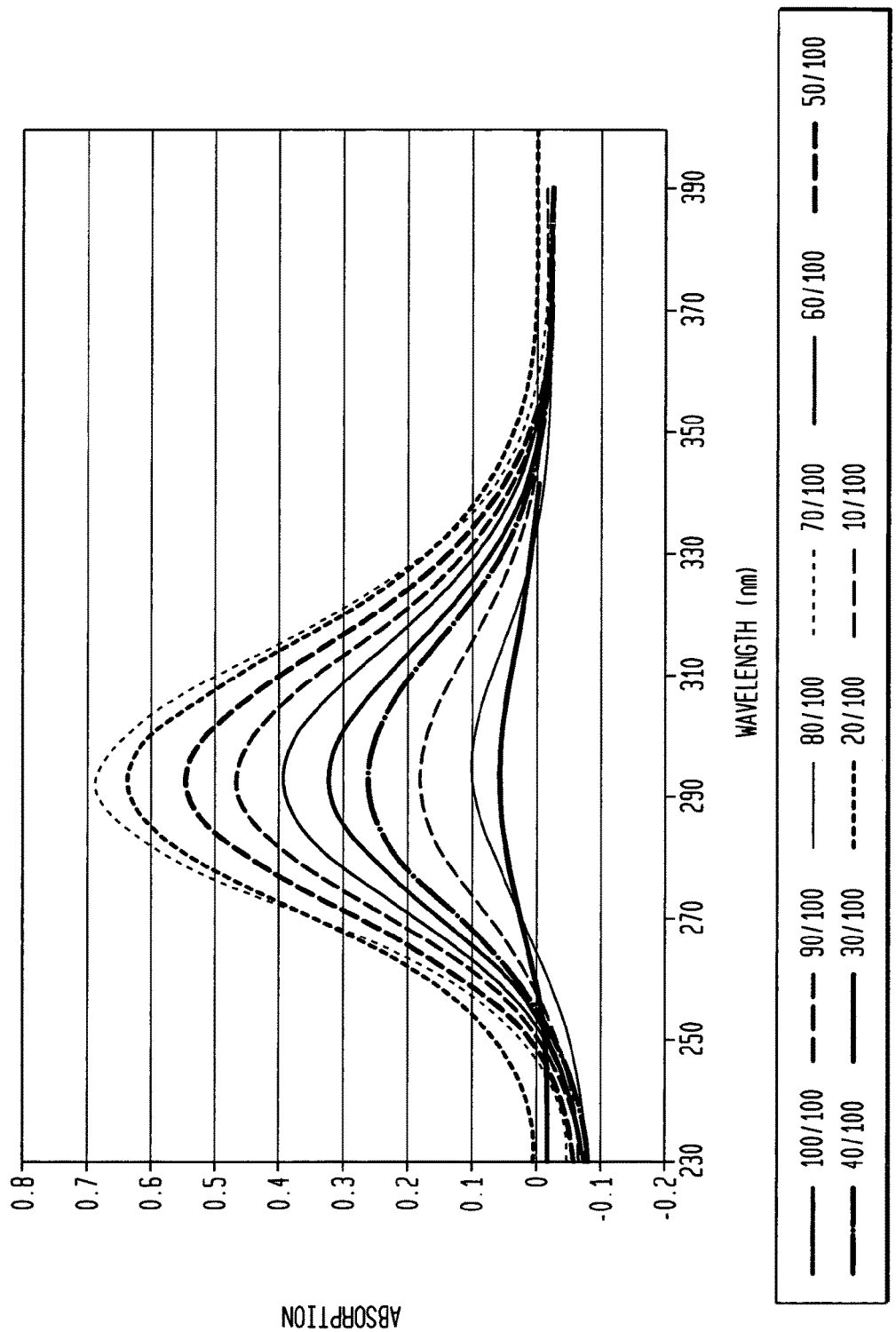
FIGS. 7-8 present data relating absorption of hypochlorite to wavelength of emitted light in accordance with one or more embodiments.

Next, the samples having various known hypochlorite concentrations underwent a spectroscopic analysis by passing UV beams of varying wavelengths through the samples. The absorption to wavelength graph that was produced is shown in FIG. 7. The hypochlorite concentration for each of the depicted absorption curves is shown in the legend to FIG. 7, for example, $70/100$ represents a 70% hypochlorite concentration for that sample. As shown in FIG. 7, peak absorbance of hypochlorite for all concentrations occurs at a wavelength of approximately 290 nm.

Figure 8:
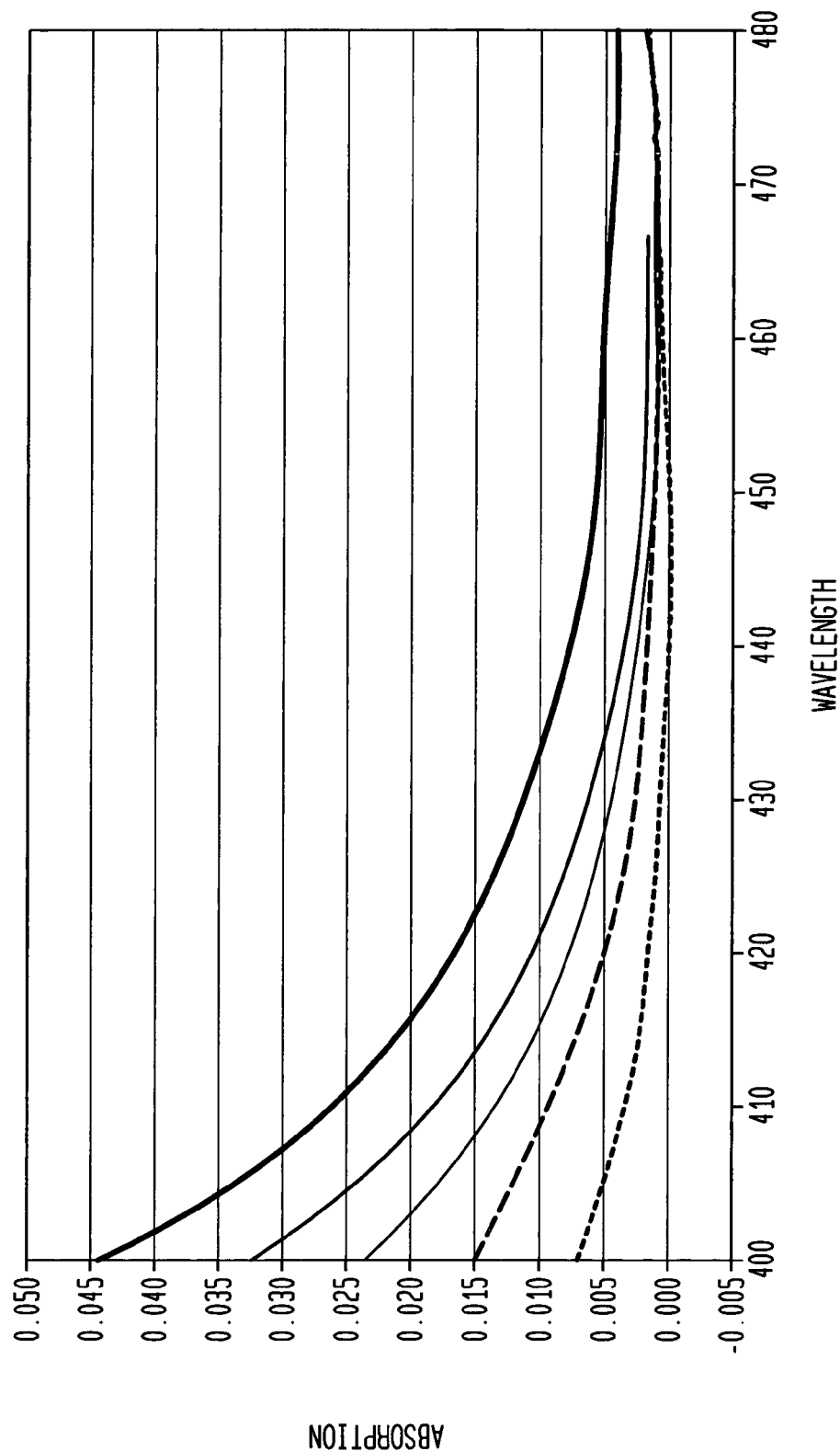

The experiment, however, went on to identify that even at wavelengths far from that of peak absorbance, the Beer-Lambert Law still applied for hypochlorite. FIG. 8 shows an absorption to wavelength graph for sodium hypochlorite at non-peak wavelengths. The absorption of hypochlorite at these wavelengths is approximately an order of magnitude less than at a peak-absorption wavelength.

Figure 9:
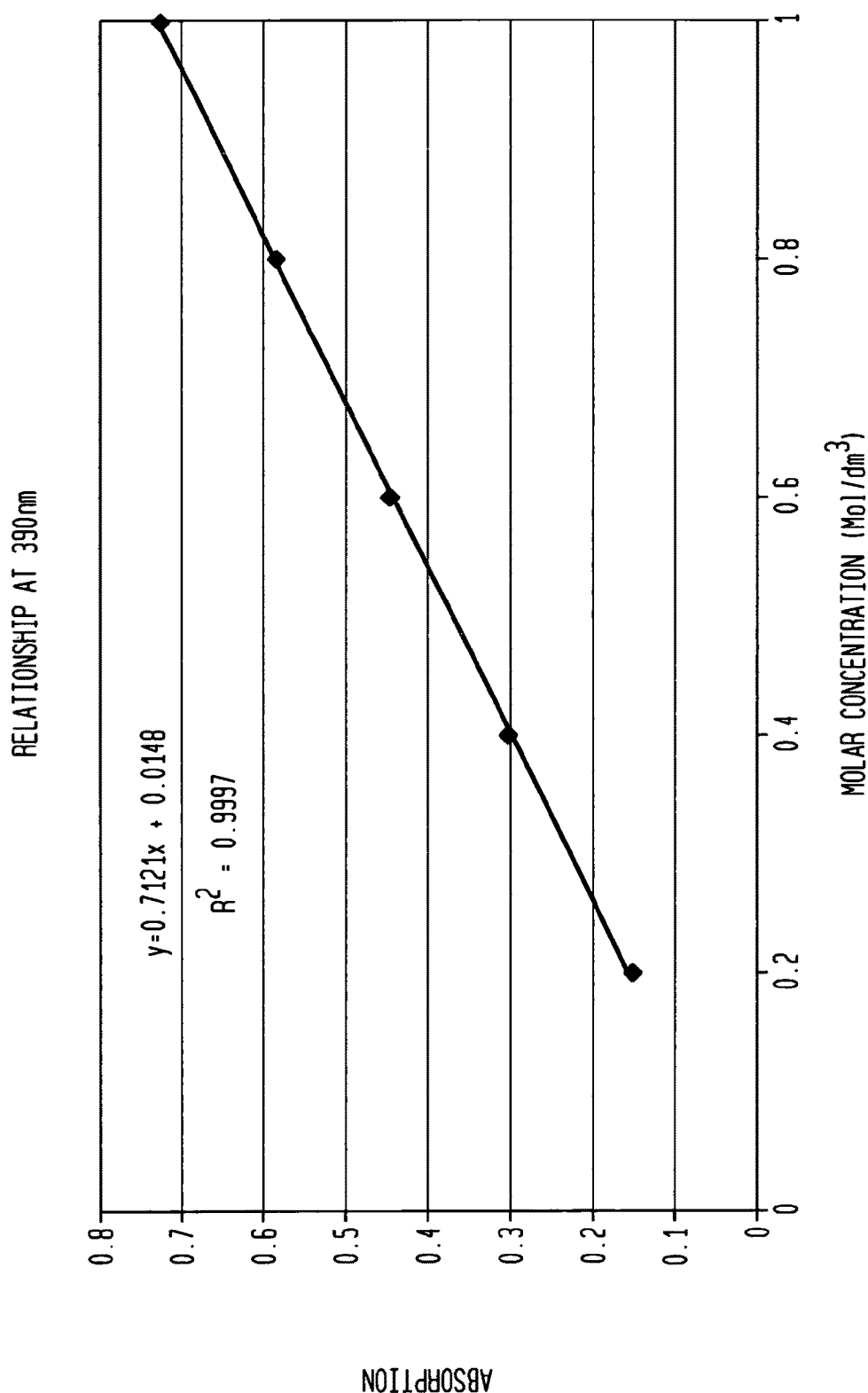
FIG. 9 presents data relating absorption of hypochlorite at 390 nm to molar concentration of hypochlorite.

FIG. 9 depicts the relationship between absorption and hypochlorite concentration at a wavelength of 390 nm, demonstrating that the Beer-Lambert Law applies even at a wavelength far from peak absorbance.

EXAMPLE 2

An emitter-detector system was constructed to accurately measure hypochlorite concentrations. A schematic of the developed system is shown in FIG. 1.

The testing appliances included a current source to power the UV LED. A simple, cost efficient mechanical solution was chosen for the splitting of the beam. This involved a custom designed PVC block which created two distinct light pathways, one going through the measured sample and one for reference purposes. Two photodiodes were placed at the end of each pathway. The current through these detectors would be the fundamental measurement for the calculation of the absorbance, according to the Beer-Lambert Law. The sensor was tested under various hypochlorite concentrations. To achieve this, several iodometric titration procedures and suitable dilutions were followed in order to cover the desirable range of hypochlorite strength (0-1%), following the steps described in Example 1, above. A wavelength of 395 nm was used.

An optional logarithmic amplifier was included to produce the logarithmic ratio that aided in making an accurate measurement of the absorbance. A microprocessor was used to translate the data into an LCD display which presented the measured hypochlorite strength in its final form, as shown in FIG. 1.

Figure 10:
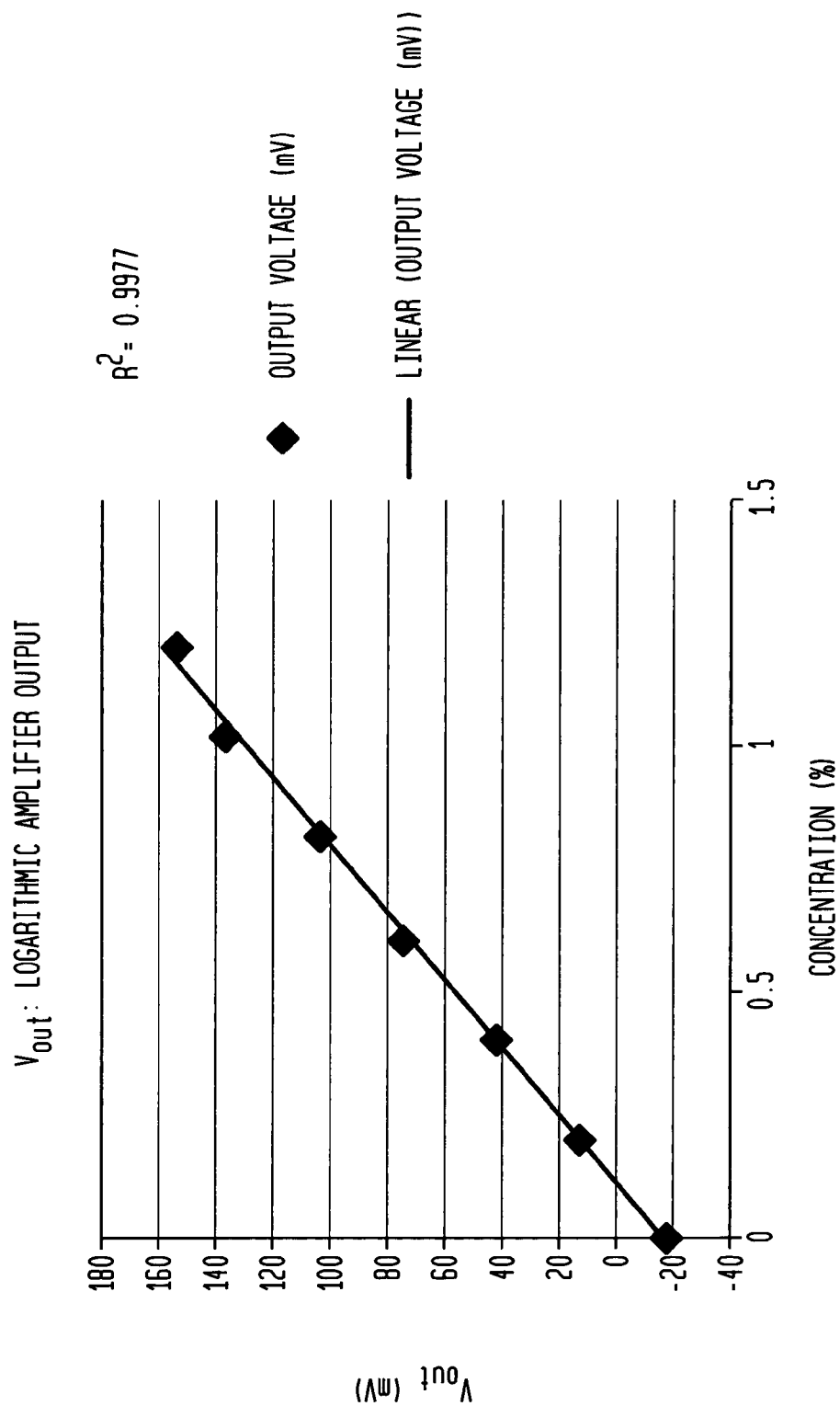
FIG. 10 presents data relating amplifier output to hypochlorite concentration in accordance with one or more embodiments.
Figure 11:
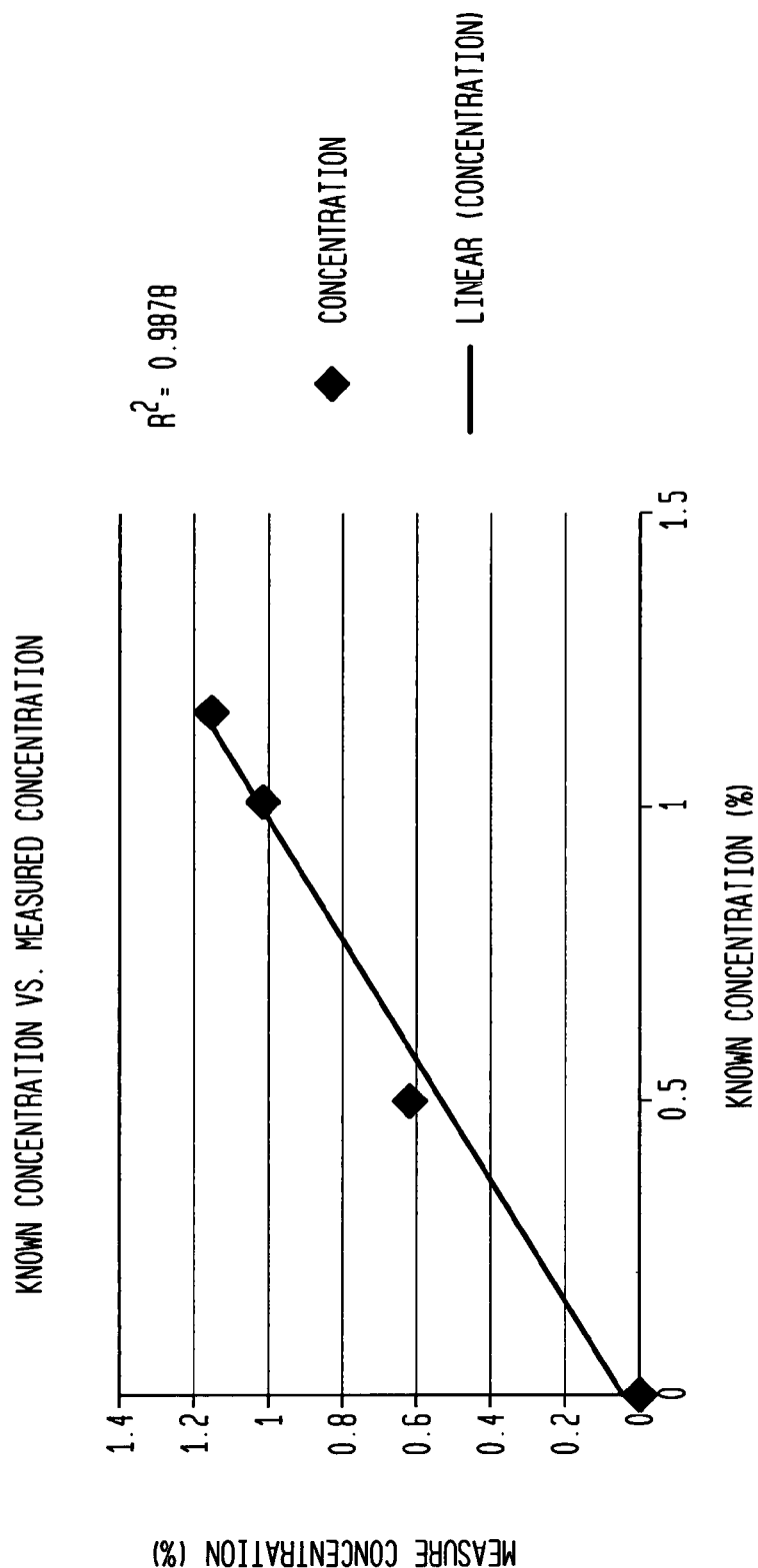
FIG. 11 presents data relating calculated hypochlorite concentration to known hypochlorite concentration in accordance with one or more embodiments.

The results are presented in FIG. 10. After the integration of the microprocessor and the LCD screen, the experiment was repeated again and the final results are shown in FIG. 11 as captured by the LCD screen.

The voltage output of the logarithmic amplifier was practically linear to the concentration of the hypochlorite strength (correlation of 0.9977), confirming that the Beer-Lambert law was still relevant at this wavelength. Last, the addition of the ADC converter and the display brought the prototype closer to a more commercial version achieving a correlation of 0.9878 between the known and the measured hypochlorite concentrations. This investigation demonstrated the successful use of a spectrophotometric sensor to measure hypochlorite strength. FIGS. 10 and 11 illustrate that the proposed sensor provides an accurate measurement of hypochlorite concentration.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only. In particular, although many of the examples presented herein involve specific combinations of method acts or system elements, it should be understood that those acts and those elements may be combined in other ways to accomplish the same objectives.

Furthermore, those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is, therefore, to be understood that the embodiments described herein are presented by way of example only and that, within the scope of any appended claims and equivalents thereto; the invention may be practiced other than as specifically described.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to any claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish claim elements.

While exemplary embodiments of the disclosure have been disclosed many modifications, additions, and deletions may be made therein without departing from the spirit and scope of the disclosure and its equivalents, as set forth in the following claims.

What is claimed is:

1. A spectrophotometric hypochlorite sensor, comprising:
   a first source of monochromatic radiation configured to provide a beam of monochromatic radiation having a wavelength in the range of about 350 nm to 410 nm and configured to produce an emitted light;
   a sample chamber configured and positioned to receive the emitted light and contain a sample comprising hypochlorite through which the emitted light passes to produce a partially absorbed light;
   a detector configured and positioned to receive the partially absorbed light and generate an input signal in response to receiving the partially absorbed light; and
   a processor configured to receive the input signal from the detector, correlate the input signal to a hypochlorite concentration of the sample, and generate an output signal indicative of the hypochlorite concentration of the sample.

2. The sensor of claim 1, wherein the first source of monochromatic radiation comprises a first light emitting diode (LED).

3. The sensor of claim 2, further comprising a first fiber optic cable configured to receive the emitted light from the first LED and transmit the emitted light to the sample chamber, and a second fiber optic cable configured to receive the partially absorbed light from the sample chamber and transmit the partially absorbed light to the detector.

4. The sensor of claim 1, wherein the first source of monochromatic radiation produces an emitted light having a wavelength that corresponds to a non-peak absorbance wavelength for hypochlorite.

5. The sensor of claim 1, wherein the first source of monochromatic radiation is configured to provide an emitted light having a wavelength of about 380 nm to about 395 nm.

6. The sensor of claim 1, wherein the detector comprises a first photodiode.

7. The sensor of claim 6, further comprising a second photodiode configured to receive a reference light from the first source of monochromatic radiation, wherein the reference light does not pass through the sample chamber.

8. The sensor of claim 1, wherein the sensor is constructed and arranged to be handheld.

9. The sensor of claim 1, wherein the sensor is configured for continuous hypochlorite strength monitoring.

10. The sensor of claim 1, wherein the sensor is configured to measure a hypochlorite concentration in the range of about 0.1% to about 15% by weight.

11. The sensor of claim 2, further comprising a second LED configured to produce an emitted light having a wavelength different than that of the first LED.

12. A method for regulating disinfection of water to be treated, comprising:
    emitting an electromagnetic beam having a first radiant power at a wavelength of about 350 nm to about 410 nm through a sample of disinfectant to produce a partially absorbed electromagnetic beam;
    measuring a second radiant power of the partially absorbed electromagnetic beam;
    calculating a concentration of the disinfectant, based, at least in part, on the first radiant power and the second radiant power; and
    adjusting a valve configured to regulate introduction of the disinfectant to the water to be treated based, at least in part, on the calculated disinfectant concentration.

13. The method of claim 12, wherein the electromagnetic beam is emitted from a light emitting diode (LED).

14. The method of claim 12, wherein the disinfectant comprises hypochlorite.

15. The method of claim 12, wherein the electromagnetic beam has a wavelength of about 380 nm to about 395 nm.

16. The method of claim 12, wherein the disinfectant concentration is a hypochlorite concentration in the range of about 0.1% to about 15% by weight.

* * * * *